United States Patent [19]

Van Daele et al.

[11] Patent Number: 4,906,643
[45] Date of Patent: Mar. 6, 1990

[54] SUBSTITUTED N-(3-HYDROXY-4-PIPERIDINYL)BENZAMIDES AS GASTROINTESTINAL AGENTS

[75] Inventors: Georges H. P. Van Daele, Turnhout; Freddy F. Vlaeminck, Lille; Karel J. Van Loon, Vosselaar, all of Belgium

[73] Assignee: Janssen Pharmaceutica N.V., Beerse, Belgium

[21] Appl. No.: 204,793

[22] Filed: Jun. 10, 1988

Related U.S. Application Data

[63] Continuation-in-part of Ser. No. 74,845, Jul. 17, 1987, abandoned.

[51] Int. Cl.$^4$ .................. C07D 211/36; C07D 211/68; C07D 401/00; A61K 31/445

[52] U.S. Cl. .................... 514/318; 546/188; 546/194; 546/208; 546/112; 546/141; 546/142; 546/143; 546/146; 546/149; 546/150; 546/153; 546/155; 546/156; 546/157; 546/158; 546/159; 546/162; 546/164; 546/165; 546/168; 546/171; 546/175; 546/174; 546/176; 546/177; 546/178; 546/179; 546/180; 546/183; 546/186; 546/187; 546/189; 546/192; 546/201; 546/215; 546/221; 546/223; 514/316; 514/326; 514/299; 514/307; 514/309; 514/310; 514/312; 514/313; 514/314; 514/317; 514/323

[58] Field of Search ............... 546/188, 194, 208, 112, 546/141, 142, 143, 146, 149, 150, 153, 155, 156, 157, 158, 159, 162, 164, 165, 168, 171, 175, 174, 176, 177, 178, 179, 180, 183, 186, 187, 189, 190, 192, 201, 215, 221, 223; 514/316, 318, 326, 299, 307, 309, 310, 312, 313, 314, 317, 323

[56] References Cited

U.S. PATENT DOCUMENTS 4,012,374  3/1977  Wade et al. .................. 546/188

FOREIGN PATENT DOCUMENTS 76530  11/1985  European Pat. Off. ........... 546/188

Primary Examiner—Mary C. Lee
Assistant Examiner—Robert C. Whittenbaugh
Attorney, Agent, or Firm—Charles J. Metz

[57] ABSTRACT

N-(3-hydroxy-4-piperidinyl)substituted benzamides, their N-oxide forms and pharmaceutically acceptable acid-addition salts having gastrointestinal motility stimulating properties, compositions containing the same, and methods of treating warm blooded animals suffering from a decreased peristalsis of the gastrointestinal system.

20 Claims, No Drawings

SUBSTITUTED N-(3-HYDROXY-4-PIPERIDINYL)BENZAMIDES AS GASTROINTESTINAL AGENTS

CROSS-REFERENCE TO RELATED APPLICATIONS

This is a continuation-in-part of application Ser. No. 74,845, filed on July 17, 1987 now abandoned.

BACKGROUND OF THE INVENTION

In the European Pat. No. 0,076,530, which corresponds to the U.S. Ser. No. 403,603 there are described N-(3-hydroxy-4-piperidinyl)benzamide derivatives which compounds are useful as stimulators of the motility of the gastrointestinal system.

The compounds of the present invention differ therefrom by the fact that the piperidinyl moiety is invariably substituted with a heterocyclyl heteroalkyl or heterocyclyl carbonyl alkyl substituent and by their favourable gastrointestinal motility stimulating properties and particularly their capability to accelerate the gastric emptying.

DESCRIPTION OF THE PREFERRED EMBODIMENTS

The invention is concerned with novel piperidinyl benzamides which can structurally be represented by the formula

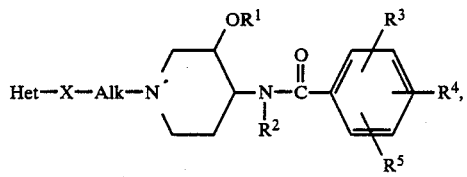

the N-oxide forms, the pharmaceutically acceptable acid addition salts and possible stereoisomeric forms thereof, wherein:

$R^1$ is hydrogen, $C_{1-6}$alkyl, aryl$C_{1-6}$alkyl, $C_{1-6}$alkylcarbonyl, amino$C_{1-6}$alkyl or mono- and di($C_{1-6}$alkyl)amino$C_{1-6}$alkyl;

$R^2$ is hydrogen or $C_{1-6}$alkyl;

$R^3$, $R^4$ and $R^5$ each independently are hydrogen, $C_{1-6}$alkyl, $C_{1-6}$alkyloxy, halo, hydroxy, cyano, nitro, amino, mono- and di-($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylaminosulfonyl, $C_{1-6}$alkylsulfinyl, $C_{1-6}$alkylsulfonyl, $C_{1-6}$alkylthio, mercapto, trifluoromethyl, aryl$C_{1-6}$alkyloxy or aryloxy;

Alk being a $C_{1-6}$alkanediyl radical;

X is O, S, NR$^6$, >C(=O) or >C(=S); said R$^6$ being hydrogen or $C_{1-6}$alkyl;

Het is a five- or six membered heterocyclic ring containing a number of heteroatoms which varies from 1 to 4, said heteroatoms being selected from the group consisting of oxygen, sulfur and nitrogen, provided that no more than two oxygens or sulfurs are present, said five- or six membered ring being optionally fused with a six membered carbocyclic ring, and when said Het is a bicyclic ring system it may optionally be substituted with up to 6 substituents, and when said Het is a monocyclic ring system it may optionally be substituted with up to 3 substituents, said substituents being selected from the group consisting of halo, hydroxy, nitro, cyano, trifluoromethyl, $C_{1-6}$alkyl, aryl$C_{1-6}$alkyl, $C_{1-6}$alkyloxy, $C_{1-6}$alkylthio, mercapto, amino, mono- and di($C_{1-6}$alkylamino), aryl$C_{1-6}$alkylamino, aminocarbonyl, mono- and di($C_{1-6}$alkylamino)carbonyl, piperidinylcarbonyl, pyrrolidinylcarbonyl, $C_{1-6}$alkyloxycarbonyl, aryl$C_{1-6}$alkyloxycarbonyl, a bivalent radical =O and =S;

provided that (i) Het is connected to X on a carbon atom, and (ii) Het is other than thienyl optionally substituted with halo or $C_{1-6}$alkyl;

wherein aryl is phenyl being optionally substituted with 1,2 or 3 substituents each independently selected from halo, hydroxy, $C_{1-6}$alkyl and $C_{1-6}$alkyloxy.

It is evident that the Het may be unsaturated or partly or completely saturated. The compounds of formula (I) wherein Het is a heterocycle which is substituted with a hydroxy, mercapto or amino radical may contain in their structure a keto-enol tautomeric system or a vinylogous system thereof, and consequently the compounds may be present in their keto forms as well as their enol form.

As used in the foregoing definitions the term "halo" is generic to fluoro, chloro, bromo and iodo. The term "$C_{1-6}$alkyl" is meant to include straight and branched saturated hydrocarbon radicals, having from 1 to 6 carbon atoms, such as, for example, methyl, ethyl, 1-methylethyl, 1,1-dimethylethyl, propyl, the four butyl isomers, the pentyl and hexyl isomers. The term "$C_{1-6}$alkanediyl" is meant to include straight and branched alkanediyl radicals, having 1 to 6 carbon atoms.

Said N-oxides of the compounds of formula (I) are meant to comprise those compounds of formula (I) wherein one or several nitrogen atoms are oxidated to the so called N-oxide, particularly those N-oxides wherein the piperidine-nitrogen is N-oxidated.

The said acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

The term acid addition salt also comprises the hydrates and solvent addition forms which the compounds of formula (I) are able to form. Examples of such forms are e.g. hydrates, alcoholates and the like.

The compounds of formula (I) have at least two asymmetric carbon atoms in their structure, namely those located in the 3- and the 4-position of the piperidine nucleus, and consequently, the substituents in the said 3- and 4-positions of the piperidine nucleus have either a trans or a cis configuration.

Pure isomeric forms of the compounds of formula (I) can be separated from the mixture by conventional separation methods. Preferably, if a specific stereoisomer is desired, said compound will be synthesized by stereoselective methods of preparation. These methods will advantageously employ enantiomerically pure starting materials.

In particular Het is either (i) an optionally substituted five- or six membered heterocyclic ring containing 1, 2 or 3 nitrogen atoms, or (ii) an optionally substituted five- or six membered heterocyclic ring containing 1 or 2 nitrogen atoms, being fused with an optionally substituted six membered carbocyclic ring, or (iii) an optionally substituted five- or six membered heterocyclic ring containing one nitrogen atom and one sulfur or oxygen atom, or (iv) an optionally substituted five- or six membered heterocyclic ring containing one nitrogen atom and one sulfur or oxygen atom, being fused with an optionally substituted six membered carbocyclic ring; wherein said Het may optionally be substituted with up to 4 substituents when Het is a bicyclic ring system (ii) or (iv), and wherein said Het may optionally be substituted with up to 2 substituents when Het is a monocyclic ring system (i) or (iii), said substituents being the same as previously described.

In more detail Het is a member selected from the group consisting of pyridinyl which is optionally substituted with one or two substituents each independently selected from halo, hydroxy, cyano, $C_{1-6}$alkyl, trifluoromethyl, $C_{1-6}$alkyloxy, aminocarbonyl, mono- and di($C_{1-6}$alkyl)aminocarbonyl, amino, mono- and di($C_{1-6}$alkyl)amino, pyrrolidinylcarbonyl and $C_{1-6}$alkyloxycarbonyl; pyrimidinyl which is optionally substituted with one or two substituents each independently selected from halo, hydroxy, cyano, $C_{1-6}$alkyl, $C_{1-6}$alkyloxy, amino and mono- and di($C_{1-6}$alkyl)amino; pyridazinyl which is optionally substituted with $C_{1-6}$alkyl or halo; pyrazinyl which is optionally substituted with one or two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl; pyrrolyl which is optionally substituted with $C_{1-6}$alkyl; pyrazolyl which is optionally substituted with $C_{1-6}$alkyl; imidazolyl which is optionally substituted with $C_{1-6}$alkyl; triazolyl which is optionally substituted with $C_{1-6}$alkyl; quinolinyl optionally substituted with up to two substituents each independently selected from halo, hydroxy, cyano, $C_{1-6}$alkyl, $C_{1-6}$alkyloxy, amino, mono- and di($C_{1-6}$alkyl)amino and trifluoromethyl; isoquinolinyl optionally substituted with up to two substituents each independently selected from halo, hydroxy, cyano, $C_{1-6}$alkyl, $C_{1-6}$alkyloxy, amino, mono- and di($C_{1-6}$alkyl)amino and trifluoromethyl; quinoxalinyl optionally substituted with up to two substituents each independently selected from $C_{1-6}$alkyl, hydroxy, halo, cyano and $C_{1-6}$alkyloxy; quinazolinyl optionally substituted with $C_{1-6}$alkyl; benzimidazolyl optionally substituted with $C_{1-6}$alkyl; indolyl optionally substituted with $C_{1-6}$alkyl; 5,6,7,8-tetrahydroquinolinyl optionally substituted with up to two substituents each independently selected from halo, hydroxy, cyano, $C_{1-6}$alkyl, $C_{1-6}$alkyloxy; amino, mono- and di($C_{1-6}$alkyl)amino and trifluoromethyl; 5,6,7,8-tetrahydroquinoxalinyl optionally substituted with up to two substituents each independently selected from $C_{1-6}$alkyl, hydroxy, halo, cyano and $C_{1-6}$alkyloxy; thiazolyl optionally substituted with $C_{1-6}$alkyl; oxazolyl optionally substituted with $C_{1-6}$alkyl; benzoxazolyl optionally substituted with $C_{1-6}$alkyl; and benzothiazolyl optionally substituted with $C_{1-6}$alkyl.

Among the heterocyclic ring systems of the above group those Het are preferred wherein Het is an optionally substituted six membered aromatic ring, with an optionally substituted pyridinyl being the most preferred Het.

Preferred compounds within the invention are those compounds of formula (I) wherein Het is a particular Het described hereinabove.

Particularly preferred compounds within the invention are those preferred compounds of formula (I) wherein $R^1$ is hydrogen or $C_{1-6}$alkyl; and/or $R^2$ is hydrogen; and/or $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylaminosulfonyl or $C_{1-6}$alkylsulfonyl; and/or X is $NR^6$, O or S.

More particularly preferred compounds of the present invention are those compounds of formula (I) wherein the substituents on the 3- and 4-position of the piperidine ring have the cis configuration.

Especially preferred compounds within the invention are those more particularly preferred compounds wherein $R^3$ being chloro, bromo, $C_{1-6}$alkylaminosulfonyl, aminosulfonyl or $C_{1-6}$alkylsulfonyl is substituted on the meta position, $R^4$ being amino is substituted on the para position; and $R^5$ being hydroxy or $C_{1-6}$alkyloxy is substituted on the ortho position.

More especially preferred compounds within the invention are those especially preferred compounds wherein X is $NR^6$ wherein $R^6$ is hydrogen or $C_{1-6}$alkyl, and Het is pyridinyl optionally substituted with up to two substituents selected from $C_{1-6}$alkyl, cyano, halo and trifluoromethyl; pyrimidinyl optionally substituted with up to two substituents selected from hydroxy, amino, mono- and di($C_{1-6}$alkyl)amino and $C_{1-6}$alkyl; pyrazinyl optionally substituted with cyano, halo, $C_{1-6}$alkyloxycarbonyl and $C_{1-6}$alkyl; or pyridazinyl optionally substituted with halo.

Most preferred compounds within the invention are selected from the group consisting of cis-4-amino-5-chloro-N-[1-[4-[(3-cyano-2-pyridinyl)amino]butyl]-3-methoxy-4-piperidinyl]-2-methoxybenzamide and the pharmaceutically acceptable acid addition salts thereof.

The compounds of formula (I) can be prepared by alkylating an intermediate of formula (III) with a piperidine of formula (II).

Het-Q$^1$ +

(III)

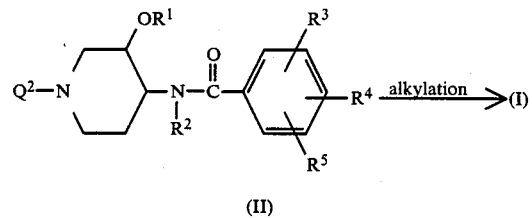

(II)

In (III) and (II), Het-Q$^1$ and Q$^2$- are selected so that a radical of formula Het-X-Alk- is formed during the alkylation reaction.

For example, the compounds of formula (I) can be prepared by N-alkylating a piperidine of formula (II)

wherein $Q^2$ is hydrogen, said piperidine being represented by the formula (II-a), with a reagent of formula (III), wherein $Q^1$ is a radical of formula -X-Alk-W, said reagent being represented by the formula (III-a).

Het—X—Alk—W +

(III-a)

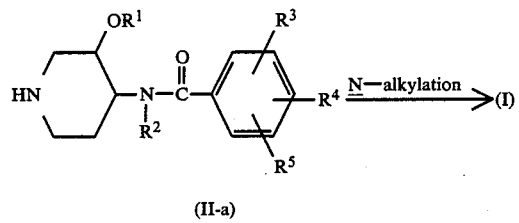

(II-a)

W as used in the reaction of (III-a) with (II-a) and in the following reaction schemes is an appropriate leaving group such as, for example, halo, preferably, chloro, bromo or iodo, or a sulfonyloxy group, e.g. methylsulfonyloxy or 4-methylphenylsulfonyloxy.

The compounds of formula (I) wherein X is O, S or $NR^6$, said X being represented by $X^1$ and said compounds by formula (I-a), can also be prepared by alkylating a piperidine of formula (II) wherein $Q^2$ is H-$X^1$-Alk-, said piperidine being represented by the formula (II-b-1), with a reagent of formula (III), wherein $Q^1$ is an appropriate leaving group $W^1$, said reagent being represented by the formula (III-b-1).

Het-$W^1$ +

(III-b-1)

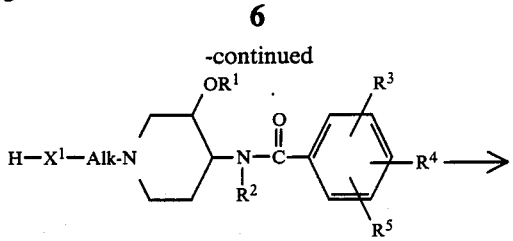

(II-b-1)

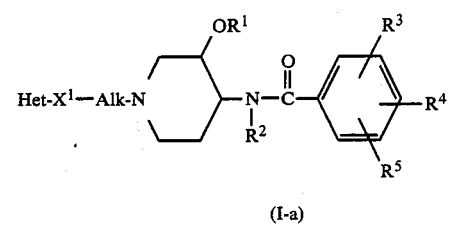

(I-a)

$W^1$ is an appropriate leaving group, such as, for example, halo, e.g. chloro or bromo, a sulfonyloxy group, or a $C_{1-6}$alkyloxy or $C_{1-6}$alkylthio group.

The compounds of formula (I-a) can alternatively be synthesized by alkylating a reagent of formula (III), wherein $Q^1$ is -$X^1$-H, said reagent being represented by the formula (III-b-2), with a piperidine of formula (II-b-2) or (II-b-3).

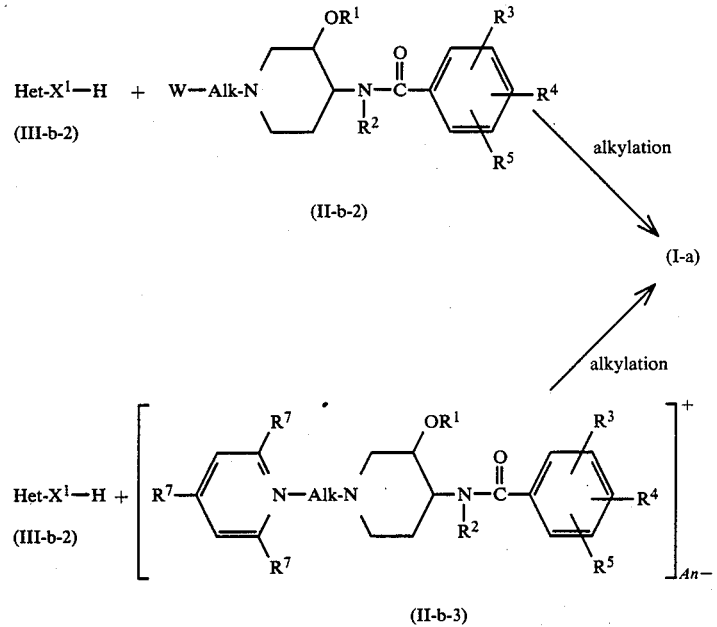

In (II-b-3) $R^7$ represents an optionally substituted phenyl radical and An⁻ represents an appropriate anion such as, for example, a halide, tetrafluoroborate, 4-methylphenylsulfonide, methanesulfonide, 4-bromophenylsulfonide and the like anions.

The alkylation reactions of (III) with (II) can be carried out according to art-known procedures, e.g. by stirring the reactants in an inert organic solvent such as, for example, an aromatic hydrocarbon, e.g. benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide, N,N-dimethylacetamide, dimethyl sulfoxide, nitrobenzene, 1-methyl-2-pyrrolidinone and the like or a mixture of two or more of such solvents.

The addition of an appropriate base such as, for example, an alkali, or an earth alkaline metal carbonate, hydrogen carbonate, hydroxide, alkoxide, hydride, amide or oxide, e.g., sodium carbonate, sodium hydrogen carbonate, potassium carbonate, sodium hydroxide, sodium methoxide, sodium hydride, sodium amide, calcium carbonate, calcium hydroxide, calcium oxide and the like, or an organic base, such as for example, a tertiary amine, e.g. N,N-diethylethanamine, N-(1-methylethyl)-2-propanamine, 4-ethylmorpholine and the like may be utilized to pick up the acid which is liberated during the course of the reaction.

In some instances the addition of a iodide salt, e.g. an alkali metal iodide is appropriate. The rate of the reaction may be enhanced by raising the temperature and in several instances the reaction may be conducted at the reflux temperature of the reaction mixture.

In the instance were (III-b-2) is an alcohol or thiol it may be advantageous to convert (III-b-2) into a metal salt thereof, preferably the sodium salt, in the usual manner, e.g., by the reaction of (III-b-2) with a metal base such as sodium hydride, sodium hydroxide and the like, and to use said metal salt subsequently in the reaction with (II-b-2) or (II-b-3).

Alternatively the above mentioned alkylation reactions of (II) with (III) may be accomplished by heating and stirring a mixture of the reactants in absence of any solvent. Said fusion reaction is preferably employed for the synthesis of (I-a) starting from (III-b-1) and (II-b-1).

The compounds of formula (I) can also be prepared by the amidation reaction of an amine of formula

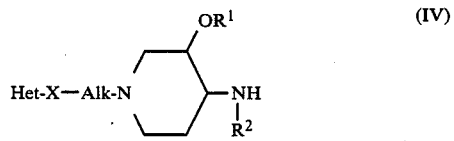

with a carboxylic acid of formula

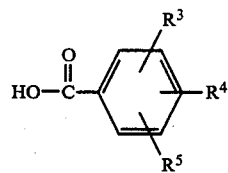

or a functional derivative thereof, such as a halide, a symmetrical or mixed anhydride or an activated ester. Said functional derivative may be generated in situ, or if desired, be isolated and further purified before reacting it with the amine of formula (IV). Functional derivatives may be prepared following art-known methods, for example, by reacting the carboxylic acid of formula (V) with thionyl chloride, phosphorous trichloride, polyphosphoric acid, phosphoryl chloride and the like, or by reacting the carboxylic acid of formula (V) with an acyl halide, e.g. acetyl chloride, ethyl carbonochloridate and the like. Or the intermediates (IV) and (V) may be coupled in the presence of a suitable reagent capable of forming amides, e.g. dicyclohexylcarbodiimide, 2-chloro-1-methylpyridinium iodide or the like reagents.

Said amidation reactions may conveniently be carried out by stirring the reactants in a suitable reaction-inert solvent such as, for example, a halogenated hydrocarbon, e.g., dichloromethane, trichloromethane and the like, an aromatic hydrocarbon, e.g., methylbenzene and the like, an ether, e.g., 1,1'-oxybisethane, tetrahydrofuran and the like or a polar aprotic solvent, e.g., N,N-dimethylformamide, N,N-dimethylacetamide and the like. The addition of a suitable base in particular a tertiary amine such as, N,N-diethylethanamine may be appropriate. The water, the alcohol or the acid which is liberated during the course of the reaction is preferably removed from the reaction mixture following art-known procedures such as, for example, by azeotropical distillation, by complexation, by salt formation and the like methods. Somewhat elevated temperatures may enhance the reaction rate. It may be necessary to routinely protect $R^3$, $R^4$ and $R^5$ amino or hydroxy groups during the course of the reaction to avoid unwanted side reactions. Suitable protecting groups comprise readily removeable groups such as $C_{1-6}$alkylcarbonyl, $C_{1-6}$alkyloxycarbonyl, aryl$C_{1-6}$alkyl and the like.

The compounds of formula (I) wherein $R^1$ is hydrogen and wherein the substituents in the 3- and 4-positions of the piperidine ring have trans configuration, said compounds being represented by the formula (I-b-1), may also be prepared by reacting a 7-oxa-3-azabicyclo[4.1.0]heptane of formula (VI) with an amide of formula (VII). The compounds of formula (I-b-1) can further be O-alkylated or O-acylated following art-known procedures thus preparing the corresponding compounds of formula (I-b-1) wherein the substituents in the 3- and 4-positions of the piperidine ring have the trans configuration and wherein $R^1$ is other than hydrogen, said $R^1$ being represented by $R^{1-a}$.

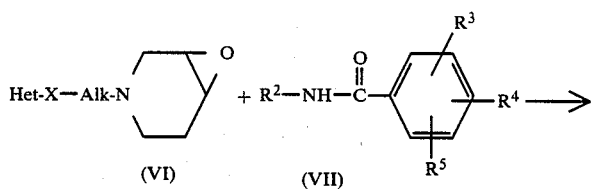

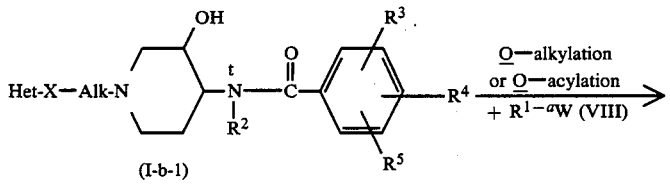

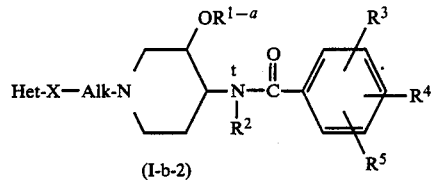

In (I-b-1) and (I-b-2) the symbol "t" indicates that the substituents in the 3- and 4-positions of the piperidine ring are in trans configuration.

The reaction of (VI) with (VII) may be conducted by stirring and, if desired, heating the reactants in a suitable reaction-inert solvent, such as, for example, an alcohol, e.g., methanol, ethanol and the like.

The O-alkylation or O-acylation reactions are conveniently conducted in an inert organic solvent such as, for example, an aromatic hydrocarbon, e.g. benzene, methylbenzene, dimethylbenzene, and the like; a lower alkanol, e.g. methanol, ethanol, 1-butanol and the like; a ketone, e.g. 2-propanone, 4-methyl-2-pentanone and the like; and ether, e.g. 1,4-dioxane, 1,1'-oxybisethane, tetrahydrofuran and the like; or a polar aprotic solvent e.g. N,N-dimethylformamide, N,N-dimethylacetamide, dimethyl sulfoxide, 1-methyl-2-pyrrollidinone, and the like. An appropriate base such as, for example, an alkali metal carbonate, sodium hydride or an organic base such as, for example, N,N-diethylethanamine or N-(1-methylethyl)-2-propanamine may be utilized to pick up the acid which is liberated during the course of the reaction. In some instances the addition of a iodide salt, preferably an alkali metal iodide, is appropriate. Somewhat elevated temperatures may enhance the rate of the reaction.

The compounds of formula (I) wherein the substituents in the 3- and 4-positions of the piperidine ring have the cis configuration, said compounds being represented by the formula (I-c), may also be prepared by the reductive N-alkylation of a piperidone of formula (IX) with an amide of formula (VII).

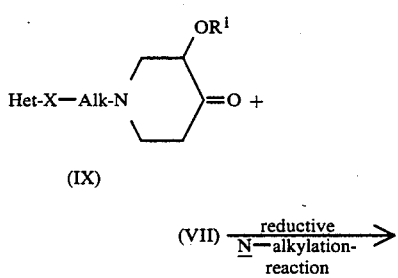

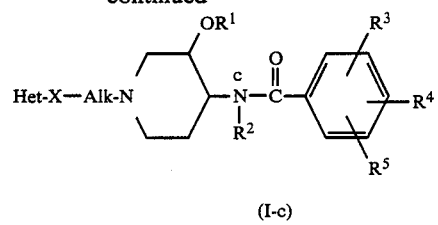

In (I-c) the symbol "c" indicates that the substituents in the 3- and 4-positions of the piperidine ring are in cis configuration. Said reductive N-alkylation reaction may conveniently be carried out by catalytically hydrogenating a mixture of the reactants in a suitable reaction-inert organic solvent according to art-known catalytic hydrogenating procedures. The reaction may be stirred and/or heated in order to enhance the reaction rate. Suitable solvents are, for example, water; alkanols, e.g. methanol, ethanol, 2-propanol; cyclic ethers, e.g. 1,4-dioxane; halogenated hydrocarbons, e.g. trichloromethane; a polar aprotic solvent e.g. N,N-dimethylformamide, dimethyl sulfoxide; or a mixture of such solvents. The term "art-known catalytic hydrogenating procedures" means that the reaction is carried out under hydrogen atmosphere in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g. thiophene and the like.

The compounds of formula (I-a) may alternatively be prepared by the reductive N-alkylation reaction of an appropriate ketone or aldehyde of formula L'=O (X), said L'=O being a compound of formula Het-X$^1$-Alk-H wherein two geminal hydrogen atoms in said Alk are replaced by =O, with a piperidine of formula (II-a).

$$L' = O + (II-a) \longrightarrow (I-a)$$
(X)

Said reductive N-alkylation reaction may conveniently be carried out by catalytically hydrogenating a mixture of the reactants in a suitable reaction-inert organic solvent according to art-known catalytic hydrogenating procedures described hereinabove for the preparation of (I-c) from (IX) and (VII). Alternatively, said reductive N-alkylation reaction may be accomplished following art-known reduction procedures, e.g. by treating a stirred and, if desired, heated mixture of the reactants with a reducing agent such as, for example, sodium cyanoborohydride, sodium borohydride, formic acid or a salt thereof, e.g. the ammonium salt.

The compounds of formula (I) can also be converted into each other following art-known procedures of functional group transformation. Some examples of such procedures will be cited hereinafter.

The compounds of formula (I) having a nitro substituent can be converted into a corresponding amine by stirring and, if desired, heating the starting nitro-compounds in a hydrogen-containing medium in the presence of a suitable amount of an appropriate catalyst in the presence of a suitable solvent. Appropriate catalysts are, for example, platinum-on-charcoal, palladium-on-charcoal, Raney-nickel and the like catalyst. Suitable solvents are, for example, methanol, ethanol and the like.

The hydrogen atoms of the amino function(s) of compounds of formula (I) may be substituted following art-known procedures such as, for example, N-alkylation, N-acylation, reductive N-alkylation and the like methods.

(1) Alkylcarbonyl, arylcarbonyl and the like groups may be introduced on the nitrogen atom by reacting the starting amine with an appropriate carboxylic acid or a derivative thereof such as, for example, an acid halide, acid anhydride and the like in a suitable solvent such as, for example, an aromatic hydrocarbon, e.g. benzene, a dipolar aprotic solvent. e.g. N,N-dimethylformamide or a mixture of such solvents.

(2) Alkyl groups may be introduced by reacting the starting amine with an alkanal or alkanone under a hydrogen atmosphere in the presence of an appropriate catalyst such as, palladium-on-charcoal, platinum-on-charcoal and the like catalysts, in suitable solvent such as, methanol, ethanol and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) containing a substituted amine may be converted into the corresponding compounds of formula (I) wherein said nitrogen bears a hydrogen following art-known methods for preparing NH groups. For example, where said nitrogen is suitable with $C_{1-6}$alkylcarbonyl, by treating the starting material with an aqueous acidic or basic solution optionally in admixture with an organic solvent.

Compounds of formula (I) containing a hydroxy function may be O-alkylated or O-acylated according to art-known procedures, e.g. by stirring the former with an appropriate acylating agent, e.g. an acid anhydride or appropriate alkylating agent, if desired, in the presence of sodium hydride.

The compounds of formula (I) containing an arylmethoxy substituent may be converted into the corresponding compounds of formula (I) containing a hydroxy function, following art-known catalytic hydrogenolysis procedures.

The compounds of formula (I) may also be converted to the corresponding N-oxide forms following art-known procedures for converting a trivalent nitrogen to its N-oxide form. Said N-oxidation reaction may generally be carried out by reacting the starting material of formula (I) with an appropriate organic or inorganic peroxide. Appropriate inorganic peroxides comprise, for example, hydrogen peroxide, an alkali metal or earth alkali metal peroxide, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like.

Said N-oxidation may be carried out in a suitable solvent such as for example, water, lower alkanols, e.g. methanol, ethanol, propanol, butanol and the like, hydrocarbons, e.g. benzene, methylbenzene, dimethylbenzene and the like, ketones, e.g. 2-propanone, 2-butanone and the like, halogenated hydrocarbons, e.g. dichloromethane, trichloromethane and the like, and the mixtures of such solvents. In order to enhance the reaction rate, it may be appropriate to heat the reaction mixture.

In all the foregoing and in the following preparations, the reaction products may be isolated from the reaction mixture and, if necessary, further purified according to methodologies generally known in the art.

Some of the intermediates and starting materials in the foregoing preparations are known compounds while others are novel. They may be prepared according to art-known methodologies of preparing said known or similarly known compounds. Some procedures for preparing such intermediates will be described hereinafter in more detail.

The intermediates of formula (II-a) can be derived from an appropriately substituted piperidine of formula (XI) by reacting the latter with a reagent of formula (V) or a functional derivative thereof, following the amidation procedures described hereinbefore for the preparation of a compound of formula (I) starting from (IV) and (V), and subsequently removing the protective group P in the thus obtained intermediate (XII) following art-known procedures, e.g. by hydrolysis in an acidic or an alkaline aqueous medium or by catalytic hydrogenation, depending upon the nature of P.

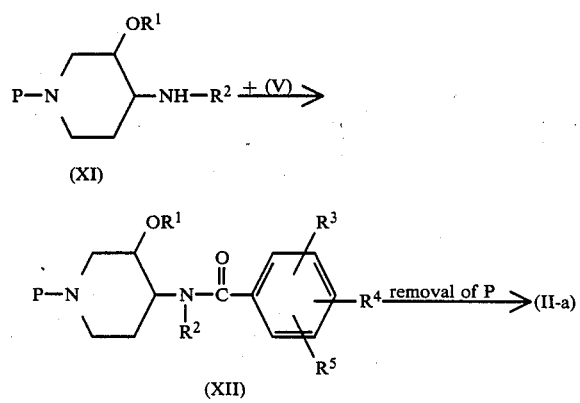

In the reaction of (XI) with (V) and in the following reaction schemes P represents a suitable protective group which is readily removeable by hydrogenation or hydrolysation. Preferred protective groups may be, for example, hydrogenolyzable groups e.g. phenylmethyl and the like, and hydrolyzable groups e.g. $C_{1-6}$alkyloxycarbonyl and the like.

Intermediates of formula (II-b-1) can be obtained by reacting a reagent HX¹-Alk-W, (XIII), or a precursor thereof with a piperidine (II-a).

For example, intermediates of formula (II-b-1) wherein $X^1$ is $NR^6$, said intermediates being represented by formula (II-b-1-a), may by synthesized by reductively N-alkylating a piperidine (II-a) with an appropriately protected amine (XIII-a) following the procedures described hereinbefore for the preparation of (I-a) starting from (X) and (II-a), and subsequently removing the protective group $P^1$ in the thus obtained intermediate (XIV) by hydrolysis in an acidic or an alkaline aqueous medium.

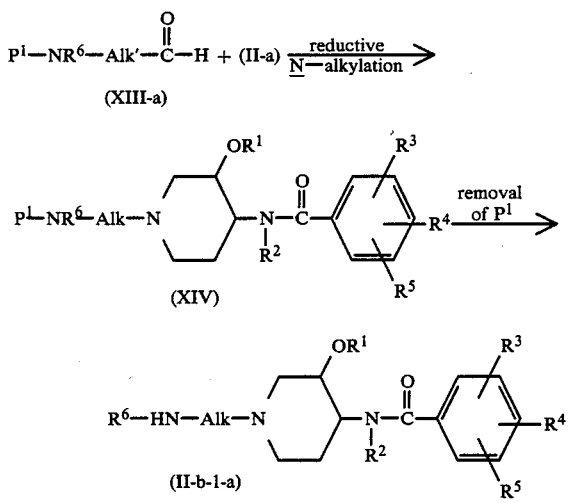

$P^1$ in the above reaction scheme is a hydrolyzable group such as, for example, $C_{1-6}$alkyloxycarbonyl. Intermediates of formula (II-b-1-a) may alternatively be prepared by reacting a piperidine (II-a) with an appropriate acetonitrile, (XIII-b), and subsequently reducing the cyano function in the thus obtained intermediate (XV).

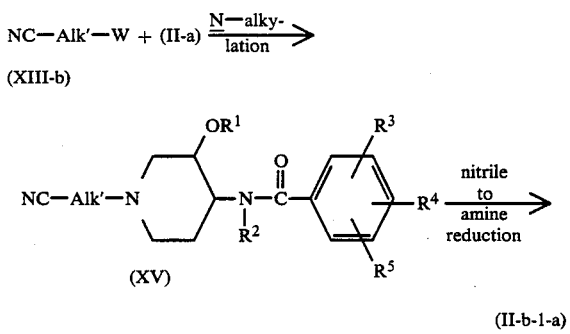

Alk' in (XIII-a), (XIII-b) and (XV) has the same meaning of Alk provided that one methylene function is missing.

The reduction of the cyano substituent in the intermediate of formula (XV) may be conducted by stirring, if desired, heating the starting cyano compounds in a hydrogen containing medium in the presence of a suitable amount of an appropriate catalyst such as, for example, platinum-on-charcoal, Raney-nickel and the like catalysts. Suitable solvents are, for example, e.g., methanol, ethanol and the like.

Or, intermediates of formula (II-b-1) where $X^1$ is oxygen and Alk is ethenyl, said intermediates being represented by (II-b-1-b), may be prepared by reacting an oxirane, (XVI), with a piperidine (II-a).

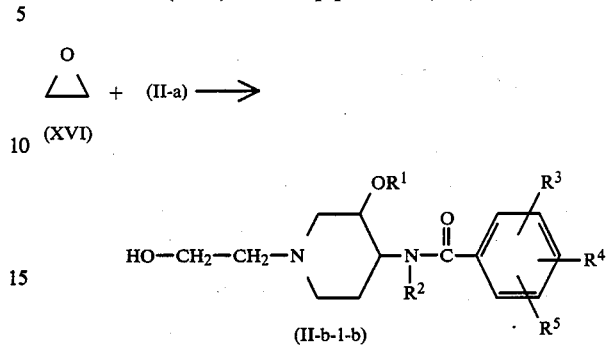

Said reaction may be conducted in a suitable solvent such as for example, an alkanone, e.g. 2-propanone, 4-methyl-2-pentanone, an ether, e.g. tetrahydrofuran, 1,1'-oxybisethane, an alcohol, e.g., methanol, ethanol, 1-butanol, a polar aprotic solvent, e.g. 4-methyl-2-pentanone, N,N-dimethylformamide, N,N-dimethylacetamide and the like.

The intermediates of formula (II-b-2) and (II-b-3) can be prepared by converting the functionality $HX^1$- of formula (II-b-1) into an appropriate leaving group.

For example, the desired intermediates of formula (II-b-3) can be prepared by reacting a piperidine of formula (II-b-1-a), with a pyrilium salt of formula (XVII).

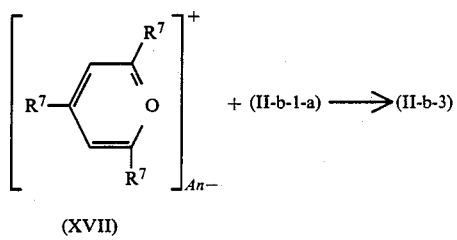

$An^-$ and $R^7$ in the pyrilium salt of formula (XVII) have the previously described meanings. Said reaction may conveniently be conducted in a suitable reaction solvent such as a halogenated hydrocarbon, e.g., di- or trichloromethane; a hydrocarbon, e.g. benzene, methylbenzene; a ketone, e.g. 2-propanone, 4-methyl-2-pentanone; or mixtures of such solvents optionally in the presence of a base such as, N,N-diethylethanamine, N-(1-methylethyl)-2-propanamine, pyridine and the like.

The desired intermediates of formula (I-b-2) wherein W represents a reactive leaving group can be obtained by converting the intermediates of formula (II-b-1-b) and their homologous into a leaving following standard procedures as known in the art. Halides are generally prepared by converting the hydroxy function with an appropriate halogenating agent such as, for example, thionyl chloride, sulfuryl chloride, pentachlorophosphorane, pentabromophoshorane, phosphoryl chloride and the like. When the leaving is a iodide it is preferably prepared from the corresponding chloride or bromide by the replacement of that halogen with iodine. Other leaving groups such as methanesulfonates and 4-methylbenzenesulfonates are obtained by the reaction of the alcohol with an appropriate sulfonyl halide such as, for example, methanesulfonyl chloride or 4-methylbenzenesulfonyl chloride respectively.

The intermediates of formula (IV) can be derived from an appropriately substituted piperidine of formula (XVIII) by alkylating the latter with an appropriate reagent, following the alkylation procedures described for (I) starting from (II) and (III), and subsequently removing the protective group P in the thus obtained intermediate following art-known procedures described hereinbefore.

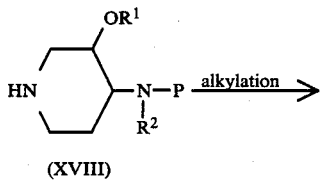

(XVIII)

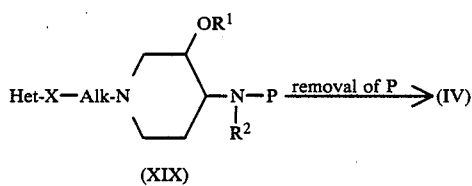

(XIX)

In general, the piperidines (XI) and (XVIII) used as starting materials, can be prepared following procedures analogous to those described in the Published Eur. patent application No. 0,076,530 which corresponds to U.S. application Ser. No. 403,603, and in Drug Development Research 8, 225–232 (1986), both incorporated herein by reference.

The intermediates of formula (XI), can easily be converted into the intermediates of formula (XVIII) for example, by introducing a protective group $P^2$ on the exocyclic nitrogen atom and selectively removing the protective group $P^1$ on the endocyclic nitrogen atom of the piperidine (XVIII).

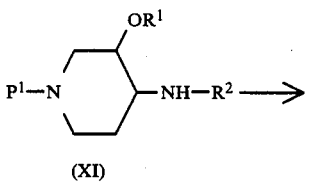

(XI)

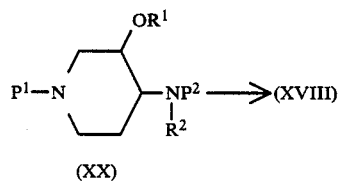

(XX)

$P^1$ and $P^2$ represent suitable protective groups as defined hereinabove which are readily introduced and removed. Suitable protective groups are, for example, hydrogenolyzable groups as $P^2$ radicals, e.g. a phenylmethyl group and the like, and hydrolyzable groups as $P^1$ radicals, e.g. a $C_{1-6}$alkyloxycarbonyl group and the like.

The compounds of formula (I) and some of the intermediates in this invention have one or more asymmetric carbon atoms in their structure. This chiral center may be present in a R- and S-configuration, this R- and S- notation being in correspondance with the rules described in J. Org. Chem., 35, 2849–2867 (1970).

Pure stereochemically isomeric forms of the compounds of formula (I) may be obtained by the application of art-known procedures. Diastereoisomers may be separated by physical separation methods such as selective crystallization and chromatographic techniques, e.g. counter current distribution, column chromatography or high performance liquid chromatography, and enantiomers may be separated according to art-known resolution methods, e.g. by the selective crystallization of the diastereomeric salts obtained with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art. Stereochemically isomeric forms of the compounds of formula (I) are naturally intended to be embraced within the scope of the invention.

The compounds of formula (I), the N-oxide forms, the pharmaceutically acceptable acid addition salts and possible stereoisomeric forms thereof possess favourable gastrointestinal motility stimulating properties. In particular they show an accelerated gastric emptying. The latter property is clearly evidenced by the results obtained in the "Gastric Emptying of a Liquid Meal in Rats"-test described hereinafter. The stimulatory effect of the subject compounds on the motility of the gastrointestinal system may further be evidenced by, for example, the "Amplification of contractions induced by trans-mural stimulation of Guinea pig ileum"-test described in The Journal of Pharmacology and Experimental Therapeutics, 234, 775–783 (1985). Similar experiments on the guinea pig ileum revealed that some compounds of formula (I) show serotonergic-$5HT_3$ antagonistic properties.

In addition the present compounds of formula (I), the N-oxide forms, the pharmaceutically acceptable acid addition salts and possible stereoisomeric forms thereof have a favourable receptor binding profile, in particularly, they do not show any apparent marked receptor-binding affinity with serotonergic-$5HT_2$, serotonergic-$5HT_1$, $\alpha_1$-adrenergic, and dopaminergic (DA) receptors.

In view of their useful gastrointestinal motility enhancing properties the subject compounds may be formulated into various forms for administration purposes. To prepare the pharmaceutical compositions of this invention, and effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of a saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the gastrointestinal system and, in particular their capacity to accelerate the gastric emptying, the subject compounds are useful to normalize or to improve the gastric and intestinal emptying.

In view of the utility of the compounds of the present invention, there is provided a method of treating warm-blooded animals suffering from a decreased peristalsis of the gastrointestinal system, which method comprises the systemic administration of an effective gastrointestinal motility stimulating amount of a compound of formula (I), a N-oxide, a pharmaceutically acceptable acid addition salt or a possible stereoisomeric form thereof, to said warm-blooded animals.

Those of skill in treating gastrointestinal disorders could easily determine the effective motility stimulating amount from the test results presented hereinafter. In general it is contemplated that an effective amount would be from 0.001 mg/kg to 10 mg/kg body weight, and more preferably from 0.01 mg/kg to 1 mg/kg body weight.

The following examples are intended to illustrate and not to limit the invention in all its aspects. Unless otherwise stated all parts therein are by weight.

EXPERIMENTAL PART

A. Preparation of Intermediates

EXAMPLE 1

To a stirred and refluxed solution of 103 parts of cis-4-amino-5-chloro-2-methoxy-N-(3-methoxy-4-piperidinyl)benzamide in 640 parts of 2-propanol were added 19.7 parts of 2-propenenitrile. The mixture was stirred overnight at reflux temperature and then over weekend at room temperature. Another portion of 3 parts of propenenitrile was added to the mixture at reflux. After stirring for 3 hours at reflux temperature, the reaction mixture was evaporated, yielding 121 parts (100%) of cis-4-amino-5-chloro-N-[1-(2-cyanoethyl)-3-methoxy-4-piperidinyl]-2-methoxybenzamide monohydrate (interm. 1).

EXAMPLE 2

To a stirred solution of 12.55 parts of cis-4-amino-5-chloro-2-methoxy-N-(3-methoxy-4-piperidinyl)benzamide in 180 parts of N,N-dimethylformamide were added 5.05 parts of N,N-diethylethanamine and 3.4 parts of 2-chloroacetonitrile. The whole was stirred for 18 hours at 50° C. The solvent was evaporated. The residue was purified by column chromatography over silica gel using a mixture of trichloromethane and methanol (95:5 by volume) as eluent. The pure fractions were collected and the eluent was evaporated. The residue was triturated in 1,1'-oxybisethane. The product was filtered off and dried, yielding 12.21 parts (86.5%) of cis-4-amino-5-chloro-N-[1-(cyanomethyl)-3-methoxy-4-piperidinyl]-2-methoxybenzamide; mp. 130.4° C. (interm. 2).

EXAMPLE 3

A mixture of 3 parts of cis-4-amino-5-chloro-N-[1-(2-cyanoethyl)-3-methoxy-4-piperidinyl]-2-methoxybenzamide and 200 parts of methanol, saturated with ammonia was hydrogenated at normal pressure and at 20° C. with 2 parts of Raney-nickel catalyst. After the calculated amount of hydrogen was taken up, the catalyst was filtered off and the filtrate was evaporated. The residue was dissolved in trichloromethane. The solution was washed with water, dried, filtered and evaporated. The residue was crystallized from acetonitrile. The product was filtered off and dried in vacuo at 60° C., yielding 0.4 parts (13%) of cis-4-amino-N-[1-(3-aminopropyl)-3-methoxy-4-piperidinyl]-5-chloro-2-methoxybenzamide; mp. 174.8 (interm. 3).

In a similar manner there were also prepared:
cis-4-amino-N-[1-(2-aminoethyl)-3-methoxy-4-piperidinyl]-5-chloro-2-methoxybenzamide; mp. 157.2° C. (interm. 4); and
cis-4-amino-N-[1-(4-aminobutyl)-3-methoxy-4-piperidinyl]-5-chloro-2-methoxybenzamide; mp. 140.0° C. (interm. 5).

EXAMPLE 4

(a) To a stirred solution of 44.3 parts of 4-(methylamino)butanol in 750 parts of trichloromethane was added dropwise a solution of 109 parts of bis(1,1'-dimethylethyl)dicarbonate in 375 parts of trichloromethane. Upon complete addition, the reaction mixture was evaporated. The residue was distilled at 26.60 Pa, yielding 50 parts (57.2%) of (1,1-dimethylethyl) (4-hydroxybutyl)methylcarbamate; bp. 120°–128° C. (interm. 6).

(b) To a stirred and cooled (<10° C.) solution of 150 parts of pyridinium dichromate in 1300 parts of dichloromethane was added dropwise a solution of 50 parts of (1,1-dimethylethyl) (4-hydroxybutyl)methylcarbamate in 91 parts of dichloromethane. Upon complete addition, stirring was continued for 3 hours in the presence of 112 parts of molecular sieves of 4A at room temperature. The reaction mixture was filtered over magnesium sulfate, washed with 1,1'-oxybisethane and the filtrate was evaporated. The residue was purified by column chromatography over silica gel using dichloromethane as eluent. The pure fractions were collected and the eluent was evaporated. The residue was taken up in methylbenzene and the whole was evaporated again, yielding 3.5 parts (6.9%) of (1,1-dimethylethyl) methyl(4-oxobutyl)carbamate as a residue (interm. 7).

(c) A mixture of 33 parts of cis-4-amino-5-chloro-2-methoxy-N-(3-methoxy-4-piperidinyl)benzamide, 30 parts of (1,1-dimethylethyl) methyl(4-oxobutyl)carbamate, 3-parts of a solution of thiophene in methanol 4% and 400 parts of methanol was hydrogenated at normal pressure and at room temperature with 5 parts of platinum-on-charcoal catalyst 5%. After the calculated amount of hydrogen was taken up, the catalyst was filtered off and the filtrate was evaporated, yielding 45.1 parts (100%) of (1,1-dimethylethyl) cis-[4-[4-[(4-amino-5-chloro-2-methoxybenzoyl)amino]-3-methoxy-1-piperidinyl]butyl]methylcarbamate as a residue (interm. 8).

(d) A mixture of (1,1-dimethylethyl) cis-[4-[4-[(4-amino-5-chloro-2-methoxybenzoyl)amino]-3-methoxy-1-piperidinyl]butyl]methylcarbamate and 250 parts of 2-propanol, saturated with hydrochloric acid was stirred and refluxed for 15 minutes. The reaction mixture was evaporated and the residue was taken up in trichloromethane. The organic layer was washed with water, saturated with ammonium hydroxide, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 33 parts (78.7%) of cis-4-amino-5-chloro-2-methoxy-N-[3-methoxy-1-[4-(methylamino)butyl]-4-piperidinyl]benzamide; mp. 129.3° C. (interm. 9).

In a similar manner there was also prepared: cis-4-amino-5-chloro-2-methoxy-N-[3-methoxy-1-[(3-methylamino)propyl]-4-piperidinyl]benzamide as a residue (interm. 10).

EXAMPLE 5

To a stirred suspension of 43 parts of cis-4-amino-N-[1-(2-aminoethyl)-3-methoxy-4-piperidinyl]-5-chloro-2-methoxybenzamide in 78 parts of dichloromethane were added 5.36 parts of N,N-diethylethanamine. A solution of 45 parts of 2,4,6-triphenylpyrylium tetrafluoroborate in 52 parts of dichloromethane was added. The whole was stirred for 3 hours and then 1.14 parts of acetic acid were added. After stirring overnight, the reaction mixture was poured into 1400 parts of 1,1'-oxybisethane. The oil was allowed to solidify while stirring. The product was filtered off, washed with water and triturated in 1,1'-oxybisethane, yielding, after filtration, 81 parts (96.6%) of cis-1-[2-[4-[(4-amino-5-chloro-2-methoxybenzoyl)amino]-3-methoxy-1-piperidinyl]ethyl]-2,4,6-triphenylpyridinium tetrafluoroborate (interm. 11).

In a similar manner there were also prepared:
cis-1-[3-[4-[(4-amino-5-chloro-2-methoxybenzoyl)amino]-3-methoxy-1-piperidinyl]propyl]- 2,4,6-triphenylpyridinium tetrafluoroborate (interm. 12); and
1-[4-[4-[(4-amino-5-chloro-2-methoxybenzoyl)amino]-3-methoxy-1-piperidinyl]butyl]-2,4-6-triphenylpyridinium tetrafluoroborate (interm. 13).

EXAMPLE 6

(a) During 4 hours, gaseous oxirane was bubbled through a stirred solution of 12.55 parts of cis-4-amino-5-chloro-2-methoxy-N-(3-methoxy-4-piperidinyl)benzamide in 60 parts of ethanol and 75 parts of water at room temperature until the starting material could no longer be detected on TLC. The reaction mixture was concentrated. The concentrate was taken up in trichloromethane. The solution was washed with water, dried filtered and evaporated. The residue was crystallized from acetonitrile. The product was filtered off and dried, yielding 9.81 parts (68.55%) of cis-4-amino-5-chloro-N-[1-(2-hydroxyethyl)-3-methoxy-4-piperidinyl]-2-methoxybenzamide; mp. 152.8° C. (interm. 14).

(b) To a stirred solution of 5.01 parts of cis-4-amino-5-chloro-N-[1-(2-hydroxyethyl)-3-methoxy-4-piperidinyl]-2-methoxybenzamide in 112.5 parts of trichloromethane were added 1.33 parts of pyridine and 2 parts of thionyl chloride. The whole was stirred and heated for 7 hours at 50° C. and subsequently stirred overnight at room temperature. The reaction mixture was washed with a sodium hydroxide solution and water. The product was extracted with trichloromethane. The extract was dried, filtered and evaporated, yielding 9 parts of cis-4-amino-5-chloro-N-[1-(2-chloroethyl)-3-methoxy-4-piperidinyl]-2-methoxybenzamide monohydrate as a residue (interm. 15).

EXAMPLE 7

(a) To a stirred and heated (±70° C.) solution of 14.44 parts of trans-4-[(phenylmethyl)amino]-3-piperidinol in 189 parts of N,N-dimethylformamide were added 5.81 parts of chloroacetonitrile. After the addition of 9.7 parts of N,N-diethylethanamine, stirring was continued overnight at 70° C. After evaporation, the residue was taken up in dichloromethane. The organic layer was washed with a sodium carbonate solution in water, dried, filtered and evaporated. The residue was purified by column chromatography over silica gel using a mixture of trichloromethane and methanol (90:10 by volume) as eluent. The pure fractions were collected and the eluent was evaporated. The residue was suspended in 2,2'-oxybispropane. The product was filtered off and dried, yielding 13.1 parts (76.2%) of trans-3-hydroxy-4-[(phenylmethyl)amino]-1-piperidineacetonitrile; mp. 113.2° C. (interm. 16).

(b) A mixture of 12 parts of trans-3-hydroxy-4-[(phenylmethyl)amino]-1-piperidineacetonitrile and 320 parts of methanol, saturated with ammonia was hydrogenated at normal pressure and at room temperature with 3 parts of Raney-nickel catalyst. After the calculated amount of hydrogen was taken up, the catalyst was filtered off and the filtrate was evaporated to dry, yielding 11.2 parts (91.6%) of trans-1-(2-aminoethyl)-4-[(phenylmethyl)amino]-3-piperidinol as a residue (interm. 17).

(c) To a stirred solution of 11.2 parts of trans-1-(2-aminoethyl)-4-[(phenylmethyl)amino]-3-piperidinol in 135 parts of ethanol were added 5.7 parts of 2-chloropyrimidine. After the addition of 8.4 parts of sodium hydrogen carbonate, stirring was continued overnight at reflux temperature. After evaporation, the residue was taken up in a mixture of dichloromethane and water. The separated organic layer was washed with water, dried, filtered and evaporated. The residue was crystallized from acetonitrile. The product was filtered off and dried, yielding 11.84 parts (80.3%) of trans-4-[(phenylmethyl)amino]-1-[2-(2-pyrimidinylamino)ethyl]-3-piperidinol; mp. 126.9° C. (interm. 18).

(d) A mixture of 10.6 parts of trans-4-[(phenylmethyl)amino]-1-[2-(2-pyrimidinylamino)ethyl]-3-piperidinol and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (90:10 by volume) as eluent. The second fraction was collected and the eluent was evaporated, yielding 6.6 parts (86.9%) of trans-4-amino-1-[2-(2-pyrimidinylamino)ethyl]-3-piperidinol as a residue (interm. 19).

B. Preparation of Final Compounds

EXAMPLE 8

A mixture of 3.47 parts of 4-chloro-1-(3-pyridinyl)-1-butanone, 4.5 parts of cis-4-amino-5-chloro-2-methoxy-N-(3-methoxy-4-piperidinyl)benzamide, 1.94 parts of N,N-diethylethanamine, 0.1 parts of potassium iodide and 67.5 parts of N,N-dimethylformamide was stirred and heated for 48 hours at 70° C. The reaction mixture was evaporated. The residue was washed with a sodium carbonate solution in water and purified by column chromatography over silica gel using a mixture of trichloromethane and methanol (90:10 by volume) as eluent. The pure fractions were collected and the eluent was evaporated. The residue was crystallized from acetonitrile. The product was filtered off and dried, yielding 1.36 parts (20%) of cis-4-amino-5-chloro-2-methoxy-N-[3-methoxy-1-[4-oxo-4-(3-pyridinyl)butyl]-4-piperidinyl]benzamide; mp. 166.2° C. (compound 1).

EXAMPLE 9

A mixture of 4.8 parts of cis-4-amino-5-chloro-2-methoxy-N-[3-methoxy-1-[4-methylamino)butyl]-4-piperidinyl]benzamide and 1.7 parts of 3-chloro-2-pyrazinecarbonitrile (described in C.A. 89; 109 367p) was molten for 30 minutes at 100° C. After cooling, the reaction mixture was taken up in a mixture of dichloromethane, water and ammonium hydroxide. The separated organic layer was washed with water, dried, filtered and evaporated. The residue was purified by column chromatography over silica gel using a mixture of trichloromethane and methanol (97:3 by volume) as eluent. The pure fractions were collected and the eluent was evaporated. The residue was suspended in 2,2'-oxybispropane. The product was filtered off and dried, yielding 4.66 parts (75.9%) of cis-4-amino-5-chloro-N-[1-[4-[(3-cyano-2-pyrazinyl)methylamino]butyl]-3-methoxy-4-piperidinyl]-2-methoxybenzamide hemihydrate; mp. 120.0° C. (compound 2).

In a similar manner there were also prepared:

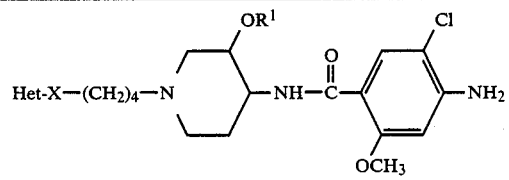

Het-X—(CH$_2$)$_4$—N piperidinyl(OR$^1$)—NH—C(=O)—C$_6$H$_2$(Cl)(OCH$_3$)—NH$_2$

| Comp. No. | Het | X | R$^1$ | isomer | mp (°C.) |
|---|---|---|---|---|---|
| 3 | 6-Cl—2-pyrazinyl | —NH— | —CH$_3$ | cis | 178.2 |
| 4 | 3-(1-pyrrolidinylcarbonyl)-2-pyridinyl | —NH— | —CH$_3$ | cis | 124.8 |
| 5 | 2-quinolinyl | —NH— | —CH$_3$ | cis | 170.7 |
| 6 | 3-H$_3$C—O—C(O)—2-pyrazinyl- | —NH— | —CH$_3$ | | 129.0 |
| 7 | 3-CN—2-pyridinyl | —N(CH$_3$)— | —CH$_3$ | cis/H$_2$O | 114.3 |
| 8 | 3-CN—5,6,7,8-tetrahydro-2-quinolinyl | —N(CH$_3$)— | —CH$_3$ | cis/0.5H$_2$O | 100.5 |
| 9 | 2-pyrimidinyl | —N(CH$_3$)— | —CH$_3$ | cis | 134.9 |
| 10 | 3-H$_3$C—2-pyrazinyl | —N(CH$_3$)— | —CH$_3$ | cis/H$_2$O | 109.5 |
| 11 | 3-(1-pyrrolidinylcarbonyl)-2-pyridinyl | —N(CH$_3$)— | —CH$_3$ | cis/H$_2$O | 126.9 |
| 12 | 3-H$_3$C—2-pyrazinyl | —NH— | —CH$_3$ | cis/0.5H$_2$O | 140.9 |
| 13 | 3-CN—6-CH$_3$O—2-quinolinyl | —NH— | —CH$_3$ | cis | 114.7 |
| 14 | 3-CN—2-pyrazinyl | —NH— | —CH$_3$ | cis/H$_2$O | 132.0 |
| 15 | 2-quinoxalinyl | —NH— | —CH$_3$ | cis | 149.8 |
| 16 | 3-CN—5,6,7,8-tetrahydro-2-quinolinyl | —NH— | —CH$_3$ | cis | 188.3 |
| 17 | 3-Cl—2-pyridinyl | —N(CH$_3$)— | —CH$_3$ | cis/H$_2$O | 102.3 |
| 18 | 2-quinoxalinyl | —N(CH$_3$)— | —CH$_3$ | cis/H$_2$O | 110.9 |
| 19 | 3-cyano-6-methoxy-2-quinolinyl | —N(CH$_3$)— | —CH$_3$ | cis/H$_2$O | 103.1 |
| 20 | 3-Cl—2-pyridinyl | —NH— | —CH$_3$ | cis | |
| 21 | 5-Cl—3-F$_3$C—2-pyridinyl | —N(CH$_3$)— | —CH$_3$ | cis/H$_2$O | 93.6 |
| 22 | 3-Cl—5-F$_3$C—2-pyridinyl | —N(CH$_3$)— | —CH$_3$ | cis | 98.1 |
| 23 | 2[H$_3$C—C(O)NH]—5-[H$_3$CO—C(O)]—4-pyrimidinyl | —NH— | —CH$_3$ | cis | |
| 24 | 5-CN—4-pyrimidinyl | —NH— | —CH$_3$ | cis | |

-continued

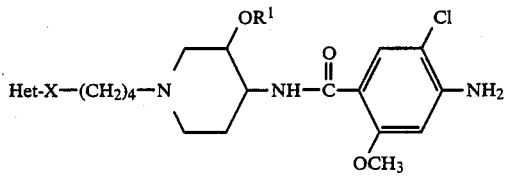

| Comp. No. | Het | X | R¹ | isomer | mp (°C.) |
|---|---|---|---|---|---|
| 25 | 3-CN—2-pyridinyl | —NH— | —CH$_2$—CH$_3$ | cis | 91.9 |
| 26 | 3-CH$_3$—5,6,7,8-tetrahydro-2-quinolinyl,N—oxide | —NH— | —CH$_3$ | cis/0.5H$_2$O | 99.8 |

EXAMPLE 10

A mixture of 8.56 parts of 2-bromo-3-methylpyrazine and 0.1 parts of potassium iodide was pulverized and 2 parts of cis-4-amino-N-[1-(2-aminoethyl)-3-methoxy-4-piperidinyl]-5-chloro-2-methoxybenzamide were added. The whole was stirred for 3 hours at 120° C. The reaction mixture was taken up in dichloromethane and water and made alkaline with ammonium hydroxide. The organic layer was separated, washed with water, dried, filtered and evaporated. The residue was purified by column chromatography over silica gel using a mixture of trichloromethane and methanol (95:5 by volume) as eluent. The first fractions was collected and the eluent was evaporated. The residue was crystallized from acetonitrile. The product was filtered off and dried, yielding 1.95 parts (36%) of cis-4-amino-5-chloro-2-methoxy-N-[3-methoxy-1-[2-[(3-methyl-2-pyrazinyl)amino]ethyl]-4-piperidinyl]benzamide; mp. 169.5° C. (compound 27).

EXAMPLE 11

A dry mixture of 1.8 parts of 2-chloro-1H-benzimidazole, 4.28 parts of cis-4-amino-N-[1-(2-aminoethyl)-3-methoxy-4-piperidinyl]-5-chloro-2-methoxybenzamide and 0.1 parts of potassium iodide was pulverized. A few drops of N,N-dimethylacetamide were added and the whole was stirred for 4 hours at 120° C. The reaction mixture was taken up in a mixture of water and dichloromethane. The whole was treated with ammonium hydroxide. The organic layer was separated, washed with water, dried, filtered and evaporated. The residue was purified by column chromatography over silica gel using a mixture of trichloromethane and methanol (90:10 by volume) as eluent. The pure fractions were collected and the eluent was evaporated. The residue was crystallized from a mixture of acetonitrile and 2,2'-oxybispropane. The product was filtered off and dried, yielding 1.06 parts (18.6%) of cis-4-amino-N-[1-[2-(1H-benzimidazol-2-ylamino)ethyl]-3-methoxy-4-piperidinyl]-5-chloro-2-methoxybenzamide; mp. 205.8° C. (compound 28).

EXAMPLE 12

A mixture of 4.6 parts of cis-4-amino-N-[1-(4-aminobutyl)-3-methoxy-4-piperidinyl]-5-chloro-2-methoxybenzamide, 1.4 parts of 2-chloropyrimidine and a few drops of N,N-dimethylacetamide was stirred overnight at 80° C. The reaction mixture was taken up in a mixture of dichloromethane, water and hydrochloric acid. The separated aqueous layer was treated with sodium carbonate and the product was extracted with dichloromethane. The extract was dried, filtered and evaporated. The residue was purified by column chromatography over silica gel using a mixture of trichloromethane, methanol and methanol, saturated with ammonia, (96:3:1 by volume) as eluent. The pure fractions were collected and the eluent was evaporated. The residue was crystallized from acetonitrile. The product was filtered off and dried, yielding 1.34 parts (24.1%) of cis-4-amino-5-chloro-2-methoxy-N-[3-methoxy-1-[4-(2-pyrimidinylamino)butyl]-4-piperidinyl]benzamide; mp. 114.8° C. (compound 29).

In a similar manner there were also prepared:
cis-4-amino-5-chloro-N-[1-[4-[[5-chloro-3-(trifluoromethyl)-2-pyridinyl]amino]butyl]-3-methoxy-4-piperidinyl]-2-methoxybenzamide monohydrate; mp. 115.9° C. (compound 30); and
cis-4-amino-5-chloro-N-[1-[4-[[3-chloro-5-(trifluoromethyl)-2-pyridinyl]amino]butyl]-3-methoxy-4-piperidinyl]-2-methoxybenzamide monohydrate; mp. 99.7°–125.2° C. (compound 31).

EXAMPLE 13

A mixture of 1.66 parts of 2-chloro-3-pyridinecarbonitrile, 4.28 parts of cis-4-amino-N-[1-(2-aminoethyl)-3-methoxy-4-piperidinyl]-5-chloro-2-methoxybenzamide, 1.3 parts of sodium carbonate and 22.5 parts of N.N-dimethylacetamide was stirred for 20 hours at 70° C. The reaction mixture was taken up in dichloromethane. The organic layer was washed with water, dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile. The product was filtered off and dried, yielding 1.19 parts (21.6%) of cis-4-amino-5-chloro-N-[1-[2-[(3-cyano-2-pyridinyl)amino]ethyl]-3-methoxy-4-piperidinyl]-2-methoxybenzamide; mp. 134.0° C. (compound 32).

In a similar manner there are also prepared:
cis-4-amino-5-chloro-N-[1-[2-[(3-chloro-2-pyridinyl)amino]ethyl]-3-methoxy-4-piperidinyl]-2-methoxybenzamide; mp. 155.8° C. (compound 33);
cis-4-amino-5-chloro-N-[1-[2-[(6-chloro-3-pyridazinyl)amino]ethyl]-3-methoxy-4-piperidinyl]-2-methoxybenzamide; mp. 228.8° C. (compound 34); and
cis-4-amino-N-[1-[3-(1H-benzimidazol-2-ylamino)propyl]-3-methoxy-4-piperidinyl]-5-chloro-2-methoxybenzamide 2-propanol(2:1); mp. 164.8° C. (compound 35).

EXAMPLE 14

A mixture of 1.17 parts of 2-chloropyrimidine, 5.56 parts of cis-4-amino-N-[1-(3-aminopropyl)-3-methoxy-4-piperidinyl]-5-chloro-2-methoxybenzamide and 2.7 parts of N,N-dimethylacetamide was stirred for 6.5 hours at 90° C. After cooling, a sodium carbonate solution was added. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from a mixture of 2-propanol and 2,2'-oxybispropane. The product was filtered off and dried, yielding 2.4 parts (35%) of cis-4-amino-5-chloro-2-methoxy-N-[3-methoxy-1-[3-(2-pyrimidinylamino)propyl]-4-piperidinyl]benzamide; mp. 158.5° C. (compound 36).

In a similar manner there were also prepared:
cis-4-amino-5-chloro-N-[1-[3-[(3-cyano-2-pyridinyl)amino]propyl]-3-methoxy-4-piperidinyl]-2-methoxybenzamide hemihydrate; mp. 125.7° C. (compound 37);
cis-4-amino-5-chloro-N-[1-[3-[(3-chloro-2-pyridinyl)amino]propyl]-3-methoxy-4-piperidinyl]-2-methoxybenzamide ethanedioate(1:1), hemihydrate; mp. 216.6° C. (compound 38);
cis-4-amino-5-chloro-N-[1-[3-[(6-chloro-3-pyridazinyl)amino]propyl]-3-methoxy-4-piperidinyl]-2-methoxybenzamide; mp. 176.8° C. (compound 39);

EXAMPLE 15

A mixture of 3.78 parts of cis-4-amino-N-[1-(4-aminobutyl)-3-methoxy-4-piperidinyl]-5-chloro-2-methoxybenzamide, 1.66 parts of 2-chloro-3-pyridinecarbonitrile, 1.58 parts of sodium carbonate and 90 parts of N,N-dimethylformamide was stirred for 24 hours at 70° C. The reaction mixture was evaporated. The residue was taken up in water and the product was extracted twice with dichloromethane. The combined extracts were washed with water, dried, filtered and evaporated. The residue was purified by column chromatography over silica gel using a mixture of trichloromethane and methanol, saturated with ammonia, (95:5 by volume) as eluent. The first fraction was collected and the eluent was evaporated. The residue was taken up in acetonitrile. The product was filtered off and dried, yielding 1.12 parts (23%) of cis-4-amino-5-chloro-N-[1-[4-[(3-cyano-2-pyridinyl)amino]butyl]-3-methoxy-4-piperidinyl]-2-methoxybenzamide monohydrate; mp. 103.4° C. (compound 40).

In a similar manner there was also prepared:
cis-4-amino-5-chloro-N-[1-[3-[(3-cyano-2-pyridinyl)methylamino]propyl]-3-methoxy-4-piperidinyl]-2-methoxybenzamide monohydrate; mp. 118.2° C. (compound 41).

EXAMPLE 16

A mixture of 1.56 parts of 2-(methylthio)-4-pyrimidinol, 3.7 parts of cis-4-amino-N-[1-(3-aminopropyl)-3-methoxy-4-piperidinyl]-5-chloro-2-methoxybenzamide and 64 parts of acetonitrile was stirred for 40 hours at reflux temperature. Another portion of 0.7 parts of 2-(methylthio)-4-pyrimidinol was added and stirring was continued over weekend at reflux temperature. The reaction mixture was evaporated. The residue was taken up in trichloromethane. The whole was washed with water, saturated with ammonium hydroxide, dried, filtered and evaporated. The residue was purified by column chromatography over silica gel using a mixture of trichloromethane and methanol, saturated with ammonia, (95:5by volume) as eluent. The pure fractions were collected and the eluent was evaporated. The residue was crystallized from acetonitrile. The product was filtered off and dried, yielding 1.82 parts (39.5%) of cis-4-amino-5-chloro-N-[1-[3-[(4-hydroxy-2-pyrimidinyl)amino]propyl]-3-methoxy-4-piperidinyl]- 2-methoxybenzamide monohydrate; mp. 134.2° C. (compound 42).

In a similar manner there was also prepared:
cis-4-amino-5-chloro-N-[1-[3-[[4-(dimethylamino)-2-pyrimidinyl]amino]propyl]-3-methoxy-4-piperidinyl]-2-methoxybenzamide; mp. 212.7° C. (compound 43)

EXAMPLE 17

A mixture of 2 parts of 2-bromothiazole and 4.28 parts of cis-4-amino-N-[1-(2-aminoethyl)-3-methoxy-4-piperidinyl]-5-chloro-2-methoxybenzamide was stirred for one hour at 60° C. The mixture solidified. It was suspended in 10 parts of pyridine and stirring was continued overnight at reflux. The reaction mixture was evaporated. The residue was taken up in a saturated sodium carbonate solution. The product was extracted with trichloromethane. The extract was dried, filtered and evaporated. The residue was purified by column chromatography over silica gel using a mixture of trichloromethane and methanol (93:7 by volume) as eluent. The pure fractions were collected and the eluent was evaporated. The residue was converted into the hydrochloride salt in 2-propanol. The salt was filtered off and the free base was liberated in the conventional manner and extracted with trichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from a mixture of acetonitrile and 2,2'-oxybispropane. The product was filtered off and dried, yielding 0.6 parts (11%) of cis-4-amino-5-chloro-2-methoxy-N-[3-methoxy-1-[2-(2-thiazolylamino)ethyl]-4-piperidinyl]benzamide; mp. 140.9° C. (compound 44).

EXAMPLE 18

A mixture of 1.9 parts of 2-chlorobenzothiazole, 3.7 parts of cis-4-amino-N-[1-(3-aminopropyl)-3-methoxy-4-piperidinyl]-5-chloro-2-methoxybenzamide and 22.5 parts of methylbenzene was stirred and refluxed overnight. 1.6 Parts of sodium carbonate were added and the whole was stirred for 4 hours at reflux temperature. The methylbenzene layer was washed with water and set aside. The precipitated product, which was formed during the reaction, was filtered off and dissolved in trichloromethane. The solution was washed with water. The combined organic layers (trichloromethane and methylbenzene layers) were dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 2.06 parts (41.2%) of cis-4-amino-N-[1-

[3-(2-benzothiazolylamino)propyl]-3-methoxy-4-piperidinyl]-5-chloro-2-methoxybenzamide; mp. 161.5° C. (compound 45).

EXAMPLE 19

To a stirred mixture of 4.28 parts of cis-4-amino-N-[1-(2-aminoethyl)-3-methoxy-4-piperidinyl]-5-chloro-2-methoxybenzamide, 1.21 parts of N,N-diethylethanamine and 150 parts of trichloromethane was added a solution of 1.5 parts of 2-chloropyrimidine in 75 parts of trichloromethane. The whole was stirred and refluxed for 80 hours. After cooling, the reaction mixture was poured into a saturated sodium carbonate solution. The product was extracted with trichloromethane. The extract was washed with water, dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile. The product was filtered off and dried, yielding 1.52 parts (29.2%) of cis-4-amino-5-chloro-2-methoxy-N-[3-methoxy-1-[2-(2-pyrimidinylamino)ethyl]-4-piperidinyl]benzamide monohydrate; mp. 123.5° C. (compound 46).

EXAMPLE 20

To a stirred solution of 1.43 parts of 3-pyridinol in 135 parts of N,N-dimethylformamide were added 0.77 parts of a sodium hydride solution 50% at a temperature below 30° C. The whole was stirred first for 1.5 hours at room temperature and then for 10 minutes at 60° C. After cooling with ice water, a solution of 5.64 parts of cis-4-amino-5-chloro-N-[1-(2-chloro-ethyl)-3-methoxy-4-piperidinyl]-2-methoxybenzamide in 135 parts of N,N-dimethylformamide was added dropwise at a temperature between 17°–20° C. Upon completion, stirring was continued first overnight at room temperature and then for 3 hours at 50° C. Another portion of 5.64 parts of cis-4-amino-5-chloro-N-[1-(2-chloroethyl)-3-methoxy-4-piperidinyl]-2-methoxybenzamide was added and the mixture was stirred for 1 hour at 50° C. After the addition of crushed ice, the reaction mixture was concentrated. The aqueous phase was extracted with trichloromethane. The combined organic layers were dried, filtered and evaporated. The residue was purified by column chromatography over silica gel using a mixture of trichloromethane and methanol (95:5 by volume) as eluent. The pure fractions were collected and the eluent was evaporated. The residue was solidified on scratching in 2,2'-oxybispropane. The product was filtered off and dried, yielding 1.38 parts (20%) of cis-4-amino-5-chloro-2-methoxy-N-[3-methoxy-1-[2-(3-pyridinyloxy)ethyl]-4-piperidinyl]benzamide monohydrate; mp. 90.2° C. (compound 47).

EXAMPLE 21

A mixture of 2.16 parts of 1H-1,2,4-triazol-5-thiol, 1.03 parts of a sodium hydride dispersion 50% and 18 parts of methylbenzene was stirred for 3 hours at room temperature. A solution of 6.3 parts of cis-1-[2-[4-[(4-amino-5-chloro-2-methoxybenzoyl)amino]-3-methoxy-1-piperidinyl]ethyl]-2,4,6-triphenylpyridinium tetrafluoroborate in 9 parts of methylbenzene was added and stirring was continued first for 4 hours at reflux temperature and then over weekend at room temperature. The whole was extracted five times with 100 parts of a hydrochloric acid solution 1N. The combined acid aqueous phases were treated with potassium hydroxide and extracted with dichloromethane. The extract was dried, filtered and evaporated. The residue was crystallized from acetonitrile. The product was filtered off and dried, yielding 1.24 parts (33%) of cis-4-amino-5-chloro-2-methoxy-N-[3-methoxy-1-[2-(1H-1,2,4-triazol-5-ylthio)ethyl]-4-piperidinyl]benzamide monohydrate; mp. 161.8° C. (compound 48).

In a similar manner there were also prepared:
cis-4-amino-5-chloro-2-methoxy-N-[3-methoxy-1-[3-(2-pyrimidinylthio)propyl]-4-piperidinyl]benzamide monohydrate; mp. 107.4° C. (compound 49);
cis-4-amino-5-chloro-2-methoxy-N-[3-methoxy-1-[2-(2-pyridinylthio)ethyl]-4-piperidinyl]benzamide monohydrate; mp. 121.5° C. (compound 50);
cis-4-amino-5-chloro-2-methoxy-N-[3-methoxy-1-[2-[(1-methyl-1H-imidazol-2-yl)thio]ethyl]-4-piperidinyl]benzamide; mp. 117.4° C. (compound 51);
cis-4-amino-5-chloro-N-[1-[2-[(4,6-dimethyl-2-pyrimidinyl)thio]ethyl]-3-methoxy-4-piperidinyl]-2-methoxybenzamide dihydrate; m.p. 105.8° C. (compound 52);
cis-4-amino-5-chloro-2-methoxy-N-[3-methoxy-1-[2-(4-pyridinylthio)ethyl]-4piperidinyl]benzamide monohydrate; mp. 121.8° C. (compound 53);
cis-4-amino-5-chloro-2methoxy-N-[3-methoxy-1-[2-(2-pyrimidinylthio)ethyl]4-piperidinyl]benzamide; mp. 176.7° C. (compound 54);
cis-4-amino-5-chloro-2-methoxy-N-[3-methoxy-1-[3-(1H-1,2,4-triazol-5-ylthio)propyl]-4-piperidinyl]benzamide monohydrate; mp. 130.4° C. (compound 55);
cis-4-amino-5-chloro-N-[1-[3-[(4,6-dimethyl-2-pyrimidinyl)thio]propyl]-3-methoxy-4-piperidinyl]-2-methoxybenzamide hemihydrate; mp. 98.0° C. (compound 56);
cis-4-amino-N-[1-[2-[(1H-benzimidazol-2-yl)thio]ethyl]-3-methoxy-4-piperidinyl]-5-chloro-2-methoxybenzamide; mp. 220.6° C. (compound 57); and
cis-4-amino-5-chloro-2-methoxy-N-[3-methoxy-1-[4-[(2-pyrimidinyl)thio]butyl]-4-piperidinyl]benzamide monohydrate; mp. 102.4° C. (compound 58).

EXAMPLE 22

A mixture of 2.8 parts of 4-pyridinethiol, 1.2 parts of a sodium hydride dispersion 50% and 45 parts of phenol was stirred for 4 hours at room temperature. Then there were added 7.5 parts of cis-1-[3-[4-[(4-amino-5-chloro-2-methoxybenzoyl)amino]-3-methoxy-1-piperidinyl]-propyl]-2,4,6-triphenylpyridinium tetrafluoroborate and 30 parts of phenol. Stirring was continued for 4 hours ar reflux. The reaction mixture was extracted five times with 100 parts of a hydrochloric acid solution 1N. The combined acid aqueous phases were treated with potassium hydroxide and extracted with dichloromethane. The extract was dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was further purified by column chromatography (HPLC) over silica gel using a mixture of dichloromethane and methanol (95:5 by volume) as eluent. The pure fractions were collected and the eluent was evaporated. The residue was crystallized from acetonitrile. The product was filtered off and dried, yielding 0.88 parts (19%) of cis-4-amino-5-chloro-2 -methoxy-N-[3-methoxy-1-[3-(4-pyridylthio)propyl]-4-piperidinyl]benzamide monohydrate; mp. 114.3° C. (compound 59).

Example 23

A mixture of 2.36 parts of 4-pyridinol, 1.2 parts of a sodium hydride dispersion 50% and 18 parts of methylbenzene was stirred for 2 hours at room temperature. A solution of 7.1 parts of cis-1-[2-[4-[(4-amino-5-chloro-2-methoxybenzoyl)amino]-3-methoxy-1-piperidinyl]ethyl]-2,4,6-triphenylpyridinium tetrafluoroborate in 9 parts of methylbenzene was added and stirring was continued first for 4 hours at reflux temperature and then overnight at room temperature. The whole was extracted five times with 100 parts of a hydrochloric acid solution 1N. The combined acid aqueous phases were treated with potassium hydroxide and extracted with dichloromethane. The extract was dried, filtered and evaporated. The residue was purified twice by column chromatography over silica gel using first a mixture of trichloromethane and methanol, saturated with ammonia, (90:10 by volume) and then a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 1.23 parts (28.3%) of cis-4-amino-5-chloro-2-methoxy-N-[3methoxy-1-[2-(4-pyridinyloxy)ethyl]-4piperidinyl]benzamide; mp. 212.2° C. (compound 60).

In a similar manner there were also prepared:
cis-4-amino-5-chloro-2-methoxy-N-[3-methoxy-1-[2-[(6-methyl-3pyridinyl) oxy]ethyl]-4piperidinyl]benzamide; mp. 131.1° C. (compound 61);
cis-4amino-5-chloro-N-[1[2-[(5-chloro-3pyridinyl)oxy]ethyl]-3-methoxy-4-piperidinyl]-2-methoxybenzamide monohydrate; mp. 178.8° C. (compound 62);
cis-4-amino-5-chloro-2-methoxy-N-[3-methoxy-1-[3-[(6-methyl-3-pyridinyl)oxy]propyl]-4-piperidinyl]benzamide monohydrate; mp. 86.7° C. (compound 63); and
cis-4-amino-5-chloro-2-methoxy-N-[3-methoxy-1-[4-(3-pyridinyloxy)butyl]-4-piperidinyl]benzamide monohydrate; mp. 101.0° C. (compound 64).

Example 24

To a stirred solution of 2.37 parts of trans-4-amino-1-[2-(2-pyrimidinylamino)ethyl]-3-piperidinol in 120 parts of trichloromethane were added 2.08 parts of 3-(trifluoromethyl)benzoyl chloride. The whole was stirred for 15 minutes in an ice bath. After the addition of 1.26 parts of N,N-diethylethanamine, stirring was continued for 18 hours and the temperature was allowed to reach room temperature. The reaction mixture was washed with a sodium carbonate solution and water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was suspended in 2,2'-oxybispropane. The product was filtered off and dried, yielding 2.07 parts (50.5%) of trans-N-[3-hydroxy-1-[2-(2-pyrimidinylamino)ethyl]-4-piperidinyl]-3-(trifluoromethyl)benzamide; mp. 148.3° C. (compound 65).

C. Pharmacological examples

The useful property of the compounds of formula (I) to accelerate the gastric emptying can be demonstrated in the following test.

Example 25: Gastric Emptying of a Liquid Meal in Rats

Gastric emptying was measured in rats according to a modified version of a method originally devised by Reynell and Spray (J. Physiol. 131: 452–456, 1956). The rats were food-deprived during 24 hours and isolated in individual cages. Water was withdrawn at the start of the experiments.

The test meal, which consisted of a warm suspension of 200 mg phenol red in 40 ml distilled water was given by oral intubation (0.4 ml/rat) half an hour after subcutaneous administration of 0.63 mg/kg of a compound of formula (I) or saline. The rats were sacrificed by cervical dislocation half an hour later. The stomach was then exposed by laparotomy, quickly ligated at he pylorus and cardia, and removed. The stomach was cut up, and its contents was extracted with 100 ml of 0.1N sodium hydroxide. The phenol red content of this extract was assayed coloremetrically at 558 nm in a spectrophotometer. Table 1 shows the individual results in extinction units following test or control injections.

TABLE 1

| Gastric Emptying of a Liquid Meal in Rats. | |
|---|---|
| Comp. No. | Gastric contents of phenol red in extinction units |
| control | 1.41 |
| 1 | 0.659 |
| 3 | 0.507 |
| 6 | 0.253 |
| 7 | 0.550 |
| 14 | 0.563 |
| 15 | 0.493 |
| 27 | 0.537 |
| 28 | 0.618 |
| 29 | 0.320 |
| 30 | 0.403 |
| 31 | 0.370 |
| 33 | 0.665 |
| 36 | 0.639 |
| 37 | 0.483 |
| 39 | 0.333 |
| 40 | 0.544 |
| 42 | 0.297 |
| 50 | 0.413 |
| 51 | 0.510 |
| 54 | 0.620 |
| 56 | 0.274 |
| 57 | 0.607 |
| 63 | 0.347 |
| 64 | 0.243 |

D. Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

Example 26: Oral Drops

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 27: Oral Solution

9 Grams of methyl 4-hydroxybenzoate and 1 gram of propyl 4-hydroxybenzoate were dissolved in 4 liters of boiling purified water. In 3 liters of the solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 28: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 29: Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

Example 30: Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 31: Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the active ingredient.

What is claimed is:

1. A compound of the formula:

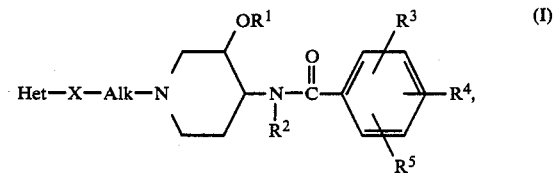

an N-oxide form, a pharmaceutically acceptable acid addition salt, or a possible stereoisomeric form thereof, wherein:

$R^1$ is hydrogen, $C_{1-6}$alkyl, aryl-$C_{1-6}$alkyl, $C_{1-6}$alkylcarbonyl, amino-$C_{1-6}$alkyl, or mono- and di($C_{1-6}$alkyl)amino-$C_{1-6}$alkyl;

$R^2$ is hydrogen or $C_{1-6}$alkyl;

$R^3$, $R^4$ and $R^5$ each independently are hydrogen, $C_{1-6}$alkyl, $C_{1-6}$alkyloxy, halo, hydroxy, cyano, nitro, amino, mono- and di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylaminosulfonyl, $C_{1-6}$alkylsulfinyl, $C_{1-6}$alkylsulfonyl, $C_{1-6}$alkylthio, mercapto, trifluoromethyl, aryl-$C_{1-6}$alkyloxy, or aryloxy;

Alk is a $C_{1-6}$alkanediyl radical;

X is O, S, $NR^6$, C(=O), or C(=S), said $R^6$ being hydrogen or $C_{1-6}$alkyl; and Het is a five- or six-membered heterocyclic ring containing one N hetero atom, said five- or six membered ring being optionally fused with a six membered carbocyclic ring, and when said Het is a bicyclic ring system it may optionally be substituted with up to 6 substituents, and when said Het is a monocyclic ring system it may optionally be substituted with up to 3 substituents, said substituents being selected from the group consisting of halo, hydroxy, nitro, cyano, trifluoromethyl, $C_{1-6}$alky, aryl-$C_{1-6}$alkyl, $C_{1-6}$alkyloxy, $C_{1-6}$alkylthio, mercapto, amino, mono- and di($C_{1-6}$alkylamino), aryl-$C_{1-6}$alkylamino, aminocarbonyl, mono- and di($C_{1-6}$alkylamino)carbonyl, piperidinylcarbonyl, pyrrolidinylcarbonyl, $C_{1-6}$alkyloxycarbonyl, aryl-$C_{1-6}$alkyloxycarbonyl, and a bivalent radical =O and =S, provided that Het is connected to X on a carbon atom; and wherein aryl is phenyl being optionally substituted with 1, 2, or 3 substituents each independently selected from halo, hydroxy, $C_{1-6}$alkyl and $C_{1-6}$alkyloxy.

2. A compound according to claim 1 wherein Het is:
   (i) an optionally substituted five- or six membered heterocyclic ring containing 1 nitrogen atom; or (ii) an optionally substituted five- or six membered heterocyclic ring containing 1 nitrogen atom, being fused with an optionally substituted six membered carbocyclic ring, wherein said Het may optionally be substituted with up to 4 substituents when Het is a bicyclic ring system (ii), and wherein said Het may optionally be substituted with up to 2 substituents when Het is a monocyclic ring system (i), said substituents being selected from the group consisting of halo, hydroxy, nitro, cyano, trifluoromethyl, $C_{1-6}$alkyl, aryl-$C_{1-6}$alkyl, $C_{1-6}$alkyloxy, $C_{1-6}$alkylthio, mercapto, amino, mono- and di($C_{1-6}$alkylamino), aryl-$C_{1-6}$alkylamino, aminocarbonyl, mono- and di($C_{1-6}$alkylamino)carbonyl, piperidinylcarbonyl, pyrrolidinylcarbonyl, $C_{1-6}$alkyloxycarbonyl, aryl-$C_{1-6}$alkyloxycarbonyl, and a bivalent radical $=O$ or $=S$, wherein aryl is phenyl being optionally substituted with 1, 2, or 3 substituents each independently selected from halo, hydroxy, $C_{1-6}$alkyl and $C_{1-6}$alkyloxy.

3. A compound according to claim 2 wherein $R^1$ is hydrogen or $C_{1-6}$alkyl; $R^2$ is hydrogen; $R^3$, $R^4$ and $R^5$ independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylsulfonyl or $C_{1-6}$alkylaminosulfonyl; and X is $NR^6$, O or S.

4. A compound according to claim 3 wherein the substituents on the 3- and 4-position of the piperidine ring have the cis configuration.

5. A compound according to claim 4 wherein $R^3$ being chloro, bromo, $C_{1-6}$alkylaminosulfonyl, aminosulfonyl or $C_{1-6}$alkylsulfonyl is substituted on the meta position, $R^4$ being amino is substituted on the para position; and $R^5$ being hydroxy or $C_{1-4}$alkyloxy is substituted on the ortho position.

6. A compound according to claim 1 wherein the compound is cis-4-amino-5-chloro-N-[1-[4-[(3-cyano-2-pyridinyl)amino]-butyl]-3-methoxy-4-piperidinyl]-2-methoxybenzamide.

7. A compound according to claim 5 wherein X is $NR^6$ wherein $R^6$ is hydrogen or $C_{1-4}$alkyl, and wherein Het is pyridinyl optionally substituted with up to two substituents selected from $C_{1-4}$alkyl, cyano, halo, and trifluoromethyl.

8. A pharmaceutical composition comprising one or more inert carriers and as active ingredient a gastrointestinal motility stimulating amount of a compound as claimed in claim 1.

9. A pharmaceutical composition according to claim 7 wherein $R^1$ is hydrogen or $C_{1-6}$alkyl; $R^2$ is hydrogen; $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylsulfonyl or $C_{1-6}$alkylaminosulfonyl; and X is $NR^6$, O or S.

10. A pharmaceutical composition according to claim 9 wherein the substituents on the 3- and 4-position of the piperidine ring have the cis configuration 11. A pharmaceutical composition according to claim 10 wherein $R^3$ being chloro, bromo, $C_{1-6}$alkylaminosulfonyl, aminosulfonyl or $C_{1-6}$alkylsulfonyl is substituted on the meta position, $R^4$ being amino is substituted on the para position; and $R^5$ being hydroxy or $C_{1-4}$alkyloxy is substituted on the ortho position.

12. A pharmaceutical composition according to claim 8 the compound is cis-4-amino-5-chloro-N-[1-[4-[(3-cyano-2-pyridinyl)amino]-butyl]-3-methoxy-4-piperidinyl]-2-methoxybenzamide.

13. A method of treating warm-blooded animals suffering from a decreased peristalsis of the gastrointestinal system, which method comprises the systemic administration to said warm-blooded animals of an effective gastrointestinal amount of a compound as claim in claim 1.

14. A pharmaceutical composition according to claim 8 wherein Het is:
(i) an optionally substituted five- or six membered heterocyclic ring containing 1 nitrogen atom; or
(ii) an optionally substituted five- or six membered heterocyclic ring containing 1 nitrogen atom, being fused with an optionally substituted six membered carbocyclic ring, wherein said Het may optionally be substituted with up to 4 substituents when Het is a bicyclic ring system (ii), and wherein said Het may optionally be substituted with up to 2 substituents when Het is a monocyclic ring system (i), said substituents being selected from the group consisting of halo, hydroxy, nitro, cyano, trifluoromethyl, $C_{1-6}$alkyl, aryl-$C_{1-6}$alkyl, $C_{1-6}$alkyloxy, $C_{1-6}$alkylthio, mercapto, amino, mono- and di($C_{1-6}$alkylamino), aryl-$C_{1-6}$alkylamino, aminocarbonyl, mono- and di($C_{1-6}$alkylamino)carbonyl, piperidinylcarbonyl, pyrrolidinylcarbonyl, $C_{1-6}$alkyloxycarbonyl, aryl-$C_{1-6}$alkyloxycarbonyl, and a bivalent radical $=O$ or $=S$, wherein aryl is phenyl being optionally substituted with 1, 2, or 3 substituents each independently selected from halo, hydroxy, $C_{1-6}$alkyl and $C_{1-6}$alkyloxy.

15. A pharmaceutical composition acording to claim 11 wherein X is $NR^6$ wherein $R^6$ is hydrogen or $C_{1-4}$alkyl, and wherein Het is pyridinyl optionally substituted with up to two substituents selected from $C_{1-6}$alkyl, cyano, halo, and trifluoromethyl.

16. A method according to claim 13 wherein Het is:
(i) an optionally substituted five- or six membered heterocyclic ring containing 1 nitrogen atom; or
(ii) an optionally substituted five- or six membered heterocyclic ring containing 1 nitrogen atom, being fused with an optionally substituted six membered carbocyclic ring, wherein said Het may optionally be substituted with up to 4 substituents when Het is a bicyclic ring system (ii), and wherein said Het may optionally be substituted with up to 2 substituents when Het is a monocyclic ring system (i), said substituents being selected from the group consisting of halo, hydroxy, nitro, cyano, trifluoromethyl, $C_{1-6}$alkyl, aryl-$C_{1-6}$alkyl, $C_{1-6}$alkyloxy, $C_{1-6}$alkylthio, mercapto, amino, mono- and di($C_{1-6}$alkylamino), aryl-$C_{1-6}$alkylamino, aminocarbonyl, mono- and di($C_{1-6}$alkylamino)carbonyl, piperidinylcarbonyl, pyrrolidinylcarbonyl, $C_{1-6}$alkyloxycarbonyl, aryl-$C_{1-6}$alkyloxycarbonyl, and a bivalent radical $=O$ or $=S$, wherein aryl is phenyl being optionally substituted with 1, 2, or 3 substituents each independently selected from halo, hydroxy, $C_{1-6}$alkyl and $C_{1-6}$alkyloxy.

17. A method according to claim 16 where $R^1$ is hydrogen or $C_{1-6}$alkyl; $R^2$ is hydrogen; $R^3$, $R^4$ and $R^5$ each independently are hydrogen, halo, $C_{1-6}$alkyloxy, amino, mono- or di($C_{1-6}$alkyl)amino, $C_{1-6}$alkylcarbonylamino, nitro, aminosulfonyl, $C_{1-6}$alkylsulfonyl or $C_{1-6}$alkylaminosulfonyl; and X is $NR^6$, O or S.

18. A method according to claim 17 wherein the substituents on the 3- and 4-position of the piperidine ring have the cis configuration.

19. A method according to claim 13 wherein the compound is cis-4-amino-5-chloro-N-[1-[4-[(3-cyano-2-pyridinyl)amino]butyl]-3-methoxy-4-piperidinyl]-2-methoxybenzamide.

20. A method according to claim 18 wherein:

$R^3$ is chloro, bromo, $C_{1-6}$alkylaminosulfonyl, aminosulfonyl, or $C_{1-6}$alkylsulfonyl and is substituted on the meta position;

$R^4$ is amino and is substituted on the para position;

$R^5$ is hydroxy or $C_{1-4}$alkyloxy and is substituted on the ortho position;

X is $NR^6$ wherein $R^6$ is hydrogen or $C_{1-4}$alkyl; and

Het is pyridinyl optionally substituted with up to two substituents selected from $C_{1-4}$alkyl, cyano, halo, and trifluoromethyl.

* * * * *